(12) United States Patent
Thompson et al.

(10) Patent No.: US 10,324,007 B2
(45) Date of Patent: Jun. 18, 2019

(54) PASSIVE DEVICE FOR VAPOR INTRUSION SAMPLING

(71) Applicant: CH2M Hill, Inc., Englewood, CO (US)

(72) Inventors: Ben Thompson, Englewood, CO (US); Michael Novak, Englewood, CO (US); Michael Niemet, Englewood, CO (US)

(73) Assignee: CH2M HILL, INC., Englewood, CO (US)

(*) Notice: Subject to any disclaimer, the term of this patent is extended or adjusted under 35 U.S.C. 154(b) by 0 days.

(21) Appl. No.: 15/724,811

(22) Filed: Oct. 4, 2017

(65) Prior Publication Data

US 2018/0095012 A1  Apr. 5, 2018

Related U.S. Application Data

(60) Provisional application No. 62/403,857, filed on Oct. 4, 2016.

(51) Int. Cl.
*G01N 1/22* (2006.01)
*G01N 33/38* (2006.01)

(52) U.S. Cl.
CPC ......... *G01N 1/2214* (2013.01); *G01N 33/383* (2013.01)

(58) Field of Classification Search
CPC ............ A61F 13/15; G01N 1/22; G01N 1/33; G01N 1/38
See application file for complete search history.

(56) References Cited

U.S. PATENT DOCUMENTS 4,356,969 A * 11/1982 Obermayer ......... A01M 1/2044
  239/56
4,413,779 A * 11/1983 Santini ................... A61L 9/127
  239/44

(Continued)

FOREIGN PATENT DOCUMENTS

WO  2018067687 A1  4/2018

OTHER PUBLICATIONS

International Search Report and Written Opinion of the International Searching Authority for International Patent Application No. PCT/US2017/055115, dated Dec. 11, 2017 (9 pages).

*Primary Examiner* — Jewel V Dowtin
(74) *Attorney, Agent, or Firm* — Dorsey & Whitney LLP

(57) ABSTRACT

Disclosed herein is a passive vapor intrusion measurement device including a barrier layer having first and second major sides; an absorbent stack disposed on a first portion of the surface of the barrier layer first major side, the absorbent stack including a first absorbent layer, an optional second absorbent layer; and spacer layer(s) disposed between the first and second (if present) absorbent layer and the barrier layer; and an adhesive disposed on a second portion of the surface of the barrier layer first major side and transversely surrounding the absorbent stack. The device is applied to a substrate in need of vapor intrusion sampling. A method of vapor intrusion analysis includes individually collecting the first and second (if present) absorbent layers after a test period; analyzing the amount of an analyte the absorbent layer(s); and subtracting the amount of the analyte in the second absorbent layer (if present) from the amount of the analyte in the first absorbent layer.

20 Claims, 7 Drawing Sheets

(56) References Cited

U.S. PATENT DOCUMENTS

| | | | | |
|---|---|---|---|---|
| 4,753,389 A | * | 6/1988 | Davis | A61L 9/01 239/56 |
| 4,889,286 A | * | 12/1989 | Spector | A61L 9/12 239/47 |
| 4,915,301 A | * | 4/1990 | Munteanu | A61L 9/01 239/45 |
| 4,917,301 A | * | 4/1990 | Munteanu | A61L 9/01 239/43 |
| 5,235,863 A | * | 8/1993 | Bailey | G01V 9/007 73/863.21 |
| 5,497,942 A | * | 3/1996 | Zingle | A61L 9/042 239/53 |
| 5,726,068 A | | 3/1998 | Rivin et al. | |
| 5,817,012 A | | 10/1998 | Schoendorfer et al. | |
| 6,018,981 A | | 2/2000 | Higgins et al. | |
| 6,613,955 B1 | | 9/2003 | Lindsay et al. | |
| 2005/0256476 A1 | | 11/2005 | Mirle et al. | |
| 2006/0004271 A1 | | 1/2006 | Peyser et al. | |
| 2009/0216168 A1 | | 8/2009 | Eckstein | |
| 2012/0028297 A1 | | 2/2012 | Zook et al. | |

\* cited by examiner

PASSIVE DEVICE FOR VAPOR INTRUSION SAMPLING

CROSS REFERENCE TO RELATED APPLICATION

The present application claims priority to U.S. Patent Application No. 62/403,857, entitled Passive Device for Vapor Intrusion Sampling, filed Oct. 4, 2016, which is hereby incorporated by reference as though fully set forth herein.

FIELD

The present invention generally relates to passive devices for measuring the concentration of compounds in a gas that is migrating through a solid surface serving as a barrier between an adjacent environmental compartment, such as a building slab, foundation, wall, floor, pavement, etc. The compounds may be volatile, organic or non-organic compounds.

BACKGROUND

Vapor intrusion, sometimes called subsurface vapor intrusion, occurs when there is a migration of volatile chemicals from contaminated groundwater or soil into an overlying building. Volatile chemicals may migrate through subsurface soils and into indoor air spaces of overlying buildings in ways similar to that of radon gas seeping into homes. Notoriously, many compounds are able to diffuse easily through concrete and other construction materials used in e.g. building foundations. The compounds can accumulate within the interior space of the building, giving rise to actual or potential health risks to building occupants.

For these reasons, measurement of vapor intrusion has become an important environmental topic. Vapor sampling of soil gas and air provides a direct measurement of compounds both beneath and within a building in order to evaluate health risks. However, the actual flux of compounds through the building slab itself can only be inferred by these measurements. Numerous published procedures and guidance documents discuss air and soil gas sampling techniques, sample analysis, and interpretation of data. Most of these publications discuss well-known active vapor sampling techniques. These methods forcefully or mechanically extract a known volume of vapor, which is hopefully a representative sample, from the soil pore space or from free air (e.g., indoor air), and are analyzed on-site or at fixed off-site laboratories following a variety of accepted sampling and analytical methods.

While passive vapor sampling is known, there is a paucity of information on passive methods to obtain accurate measurements in a vapor intrusion application. While some passive vapor sampling devices are known, they tend to be complicated, must be assembled on site from multiple components, and must be carefully situated in an attempt to avoid contamination from non-target sources which destroys the accuracy of the test.

Passive vapor sampling for clothing is known; see e.g. U.S. Pat. No. 5,726,068 describing pouch-like vapor detecting devices. Such devices will not work in a vapor intrusion application—that is, where vapors issuing from the ground must be quantified and separated from ambient vapors present in a building or other space arising from sources other than the ground. This is because the clothing-bound pouch devices measure compounds that arrive via diffusion of ambient air. Such a device does not differentiate volatiles issuing from the ground from those arising from other sources.

An exemplary type of passive sampling device specifically for vapor intrusion is described in U.S. Pat. No. 6,018,981. A rigid, dome shaped cover includes a weighted ring that is placed around the dome to hold the dome against a floor. A container of absorptive material is placed under the dome to absorb vapors. While in theory such an arrangement may work to accurately measure vapors issuing only from the ground, an uneven floor destroys the usefulness of such a device: if the rigid dome is not completely seated (sealed) against the floor, ambient air will leak into the dome. Such leakage destroys the accuracy of any measurement of vapors obtained from the absorbent. Since many concrete floors are less than perfectly planar, such a device has extremely limited utility. Additionally, multiple equipment components are required to assemble the sampling device, which complicates its use.

U.S. Pat. No. 6,018,981 illustrates the challenge in designing passive vapor intrusion devices. Specifically, such devices must accurately measure vapors issuing only from the ground, and must exclude ambient vapors arising from other sources, such as vapors previously issued and present in the atmosphere proximal to the device. While a passive measuring device may be placed subsurface to effectively eliminate above-ground ambient vapors, such an approach is not always possible or practical. Surface contact devices are needed in such applications. We are unaware of any passive vapor intrusion surface devices or methods that completely exclude measurement of ambient vapor sources in practical, real world situations where imperfect exclusion of ambient vapors may be operative.

Thus, there is a need in the industry for a passive vapor sampling device that accurately and repeatably measures vapor intrusion for a range of compounds, including volatile, organic and non-organic compounds, and under a wide range of site conditions. There is a need in the industry for devices, methods of deployment thereof, and analytical measurements taken therefrom that are simple to use, repeatable, accurate, and inexpensive to obtain. There is a need in the industry for a passive vapor intrusion device and method of vapor intrusion quantification that excludes the contribution of ambient vapors in the quantification of vapor intrusion.

SUMMARY

Disclosed herein is a passive vapor intrusion measurement device. The device includes a substantially planar barrier layer having first and second major sides; an absorbent stack disposed on a first portion of the surface of the barrier layer first major side, the absorbent stack including a first absorbent layer, a second absorbent layer, and a first spacer layer disposed between first and second absorbent layers; and an adhesive disposed on a second portion of the surface of the barrier layer first major side and transversely surrounding the absorbent stack. In some embodiments, the device includes a second spacer layer situated between the second absorbent layer and the barrier layer.

A passive vapor intrusion sampling device is disclosed. The device includes a barrier layer having first and second major sides, and an absorbent stack disposed over a first portion of the surface of the first major side of the barrier layer, and an adhesive layer disposed on a second portion of the surface area of the first major side of the barrier layer and transversely surrounding the absorbent stack. The absorbent stack includes a first absorbent layer, and a first spacer layer disposed between the first absorbent layer and the barrier layer. In some embodiments, the device may further include a second absorbent layer and a second spacer layer disposed between the first and second absorbent layers. In some embodiments, the barrier layer is impermeable to an analyte selected for vapor intrusion analysis. In some embodiments, the adhesive layer is disposed substantially over the entirety of the surface of the first major side of the barrier layer.

In some embodiments, the first portion of the surface of the first major side of the barrier layer is exclusive of the second portion of the surface of the first major side of the barrier layer. In some embodiments, the first and second absorbent layers comprise substantially the same absorbent material, and the absorbent material is present in substantially the same amount in the first and second absorbent layers. In some embodiments, the first and second absorbent layers comprise different absorbent material. The absorbent material may be present in substantially the same amount in the first and second absorbent layers. The absorbent material may be present in different amounts in the first and second absorbent layers. In some embodiments, the first absorbent layer comprises activated carbon. In some embodiments, the first and/or second absorbent layers comprise activated carbon. In some embodiments, the partition coefficient of the first absorbent layer and the second absorbent layer is 100 or greater as to between the substrate and the absorbent layers. In some embodiments, the device is a single unit.

Disclosed herein is a method of passive vapor intrusion measurement. In some aspects, the method includes applying a passive vapor sampling device according to embodiments disclosed herein to the surface of a solid substrate. The applying includes substantially contacting the first absorbent layer of the device with the substrate surface and forming an adhesively sealed interface therewith, the adhesively sealed interface transversely surrounding the absorbent stack of the passive vapor sampling device. The method further includes allowing a selected period of time to elapse and then removing the passive vapor sampling device from the substrate surface. The method further includes collecting the first absorbent layer and analyzing the amount of a selected analyte in the first absorbent layer. The method further includes calculating the vapor intrusion mass flux measured by the device based on the mass of compound absorbed, time of application, and size of exposed absorbent layer.

In some embodiments of the method, the selected period of time is about 10 minutes to 1 month. In some embodiments, the substrate is a solid surface. In some embodiments, the substrate is concrete or cement. In some embodiments, the solid surface comprises concrete, cement, tile, or a combination of two or more thereof. In some embodiments, the solid surface is a floor, slab, wall or ground surface. In some embodiments, the substrate is part of a building. In some embodiments, the substrate is in contact with the ground.

Disclosed herein is a method of passive vapor intrusion measurement. The method includes applying a passive vapor sampling device according to embodiments disclosed herein to the surface of a solid substrate. The applying includes substantially contacting the first absorbent layer of the device with the substrate surface and forming an adhesively sealed interface therewith, the adhesively sealed interface transversely surrounding the absorbent stack of the passive vapor sampling device. The method further includes allowing a selected period of time to elapse and removing the passive vapor sampling device from the substrate surface. The method further includes collecting the first and second absorbent layers. The method further includes analyzing the amount of a selected analyte in the first absorbent layer and analyzing the amount of the selected analyte in the second absorbent layer. The method further includes subtracting the amount of the compound in the second absorbent layer from the amount of the compound in the first absorbent layer. The method further includes calculating the vapor intrusion mass flux measured by the device based on the mass of compound absorbed, time of application, and size of exposed absorbent layer.

In some embodiments of the method, the selected period of time is about 10 minutes to 1 month. In some embodiments, the substrate is concrete or cement. In some embodiments, the substrate is part of a building. In some embodiments, the substrate is in contact with the ground.

Also disclosed herein is a method of passively sampling vapor intrusion of a selected analyte(s). The method includes applying a passive vapor intrusion measurement device to a solid substrate in need of vapor intrusion analysis, wherein the applying includes substantially contacting the first absorbent layer with the substrate surface; allowing a period of time (the test period) to elapse while leaving the device applied to the substrate; removing the device from the substrate surface; individually collecting the first and second absorbent layers; analyzing the amount of the analyte in the first absorbent layer; analyzing the amount of the analyte in the second absorbent layer; and subtracting the amount of the analyte in the second absorbent layer from the amount of the analyte in the first absorbent layer.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1A:
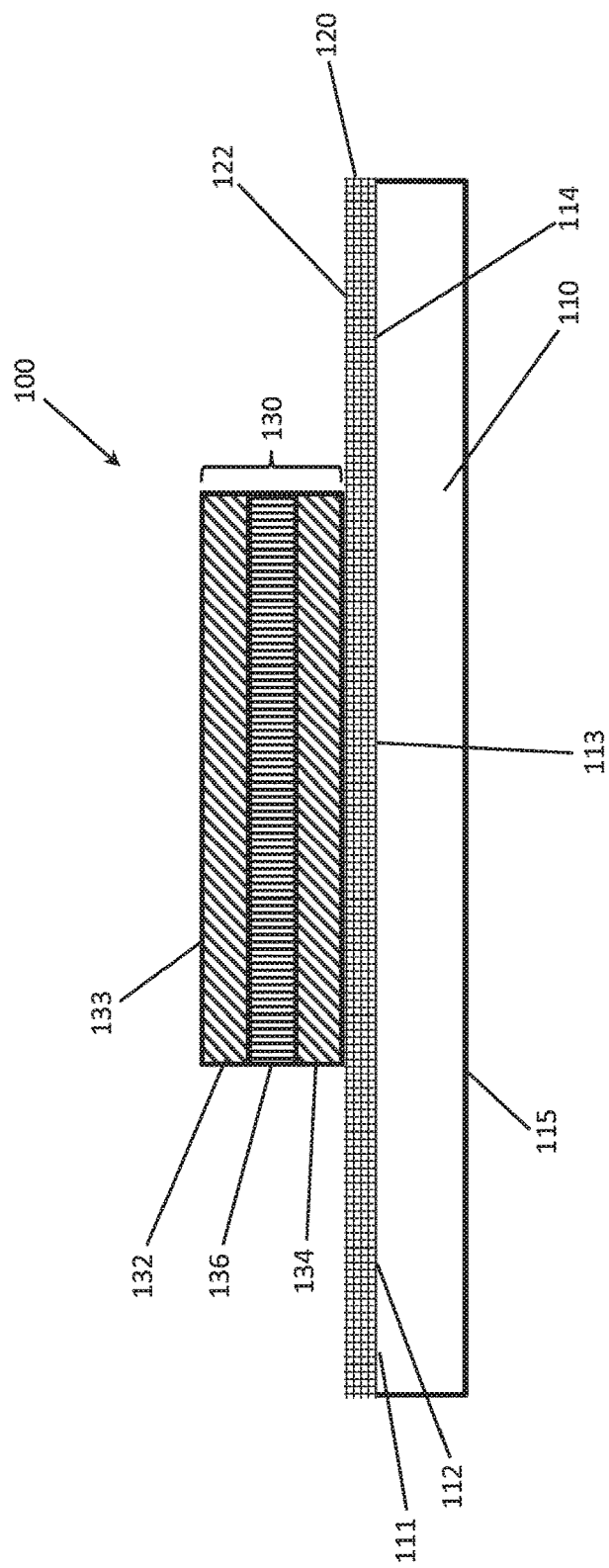
FIG. 1A is a schematic side view of a vapor intrusion device.

Although the present disclosure provides references to preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety and for all purposes. The materials, methods, and examples disclosed herein are illustrative only and not intended to be limiting.

As used herein, the term "barrier layer" means a substantially solid, planar material that is substantially impermeable to an analyte. By "substantially impermeable" it is meant that the barrier layer allows less than 10% of the selected gaseous compound to pass through relative to surrounding environment.

As used herein, the term "analyte" or "selected analyte" means a compound that has sufficient volatility to partition from a source to the gaseous state and migrate in the gaseous state to contact a passive vapor intrusion device, further wherein the compound is selected or targeted for vapor intrusion analysis.

As used herein, the term "absorb" means absorb, adsorb or both, without regard to which mechanism is actually operable.

As used herein, the term "vapor absorbent layer" or "absorbent layer" means a substantially continuous layer of substantially uniform thickness and including a material that absorbs an analyte, further wherein the material has a high affinity for the analyte.

As used herein, the term "high affinity" means that an analyte would much rather stay bound in the absorbent layer versus the environment adjacent to the absorbent layer. An absorbent with a high affinity for a specific analyte would retain at least 99% of the mass on the absorbent layer versus the surrounding environment at equilibrium. This ratio may be referred to herein as the "partition coefficient". Thus, it may be said that an absorbent having high affinity for a specific analyte is an absorbent having a partition coefficient of 100 or greater with respect to that analyte and the media contacting the absorbent.

As used herein, the term "vapor intrusion substrate" or more generally in context "substrate" means any solid material that is undergoing or is suspected of undergoing vapor intrusion and to which an adhesive bond can be formed. A substrate in need of vapor intrusion sampling or measurement includes a solid surface that is undergoing or suspected of undergoing vapor intrusion. Vapor intrusion substrates may include one or more of cement, concrete, rock or stone, wood, glass or ceramic materials, and the like. In some embodiments the vapor intrusion substrate is a man-made building, building portion, or similar construction having a foundation or floor surface exposed to the atmosphere.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of non-limiting examples thereof, planarity or planar disposition, flexibility, partition coefficient, rate, solubility, temperature, and the like; intended values include thickness, yield, weight, concentration, and the like. The effect on methods that are modified by "substantially" include the effects caused by variations in type or amount of materials used in a process, variability in machine settings, the effect of one or more ambient conditions on a process, and the like wherein the manner or degree of the effect does not negate one or more intended properties or results; and like proximate considerations. Where modified by the term "substantially" the claims appended hereto include equivalents to these types and amounts of materials.

Discussion

Passive vapor intrusion analysis is the quantification of one or more analytes, each of the analytes having sufficient volatility to partition from a source to the gaseous state and migrate in the gaseous state to contact a passive vapor intrusion device. The passive vapor intrusion devices of the invention are suitable to apply in direct contact with a solid surface or substrate surface through which one or more analytes are migrating or are suspected of migrating. The surface may be a solid surface serving as a barrier between an adjacent environmental compartment, such as a building slab, foundation, wall, floor, pavement, etc. After applying a device to such a surface and allowing the device to remain applied for a period of time, the vapor intrusion devices of the invention may be used to quantify the amount of the analyte that has migrated through the solid surface.

Passive Vapor Intrusion Device

FIG. 1A is schematic side view of one embodiment of a passive vapor intrusion device 100. Device 100 includes a substantially planar barrier layer 110 having a first major side 111 and a second major side 115 defining a thickness therebetween. First major side 111 has surface 112. Barrier layer 110 is substantially impermeable to one or more analytes. Device 100 further includes absorbent stack 130 situated over a first portion 113 of surface 112. First portion 113 of surface area 112 is less than the entirety of surface area 112. Absorbent stack 130 includes first absorbent layer 132 having first absorbent layer surface 133, second absorbent layer 134, and first spacer layer 136 disposed between first absorbent layer 132 and second absorbent layer 134 such that there is substantially no physical contact between first absorbent layer 132 and second absorbent layer 134. In the embodiment shown, layers 132, 136, 134 are substantially coextensive relative to each other. In some embodiments, first spacer layer 136 extends past the edges of absorbent layers 132, 134. In some embodiments, absorbent stack 130 includes only a single absorbent layer 132 (see also FIG. 5).

Device 100 further includes adhesive layer 120 disposed over a second portion 114 of surface area 112. Second portion 114 of surface area 112 is substantially the entirety of surface area 112 as shown in the exemplary but non-limiting embodiment of FIG. 1A. That is, adhesive layer 120 substantially covers surface area 112 and is further disposed between barrier layer 110 and absorbent stack 130. Thus, in the embodiment of FIG. 1A, barrier layer 110 is contiguous to adhesive layer 120; adhesive layer 120 is contiguous to absorbent stack 130 first absorbent layer 132; first absorbent layer 132 is contiguous to first spacer layer 136; and first spacer layer 136 is contiguous to second absorbent layer 134.

Figure 1B:
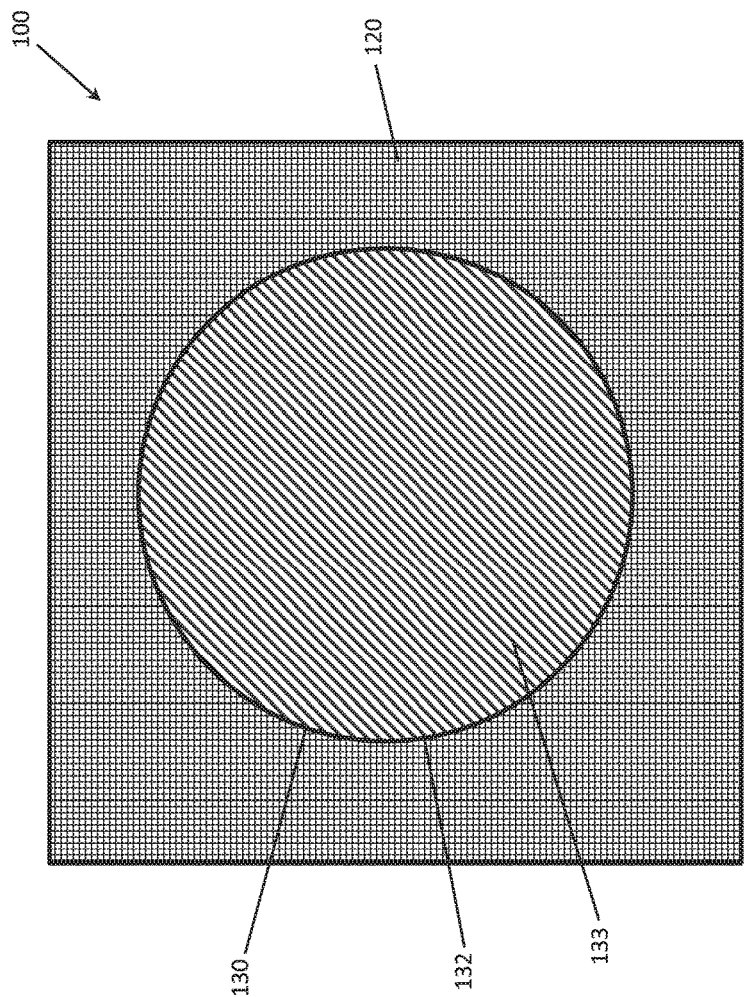
FIG. 1B is a schematic top view of the device of FIG. 1A.

FIG. 1B is a top view of device 100 shown in FIG. 1A. The overall shape of device 100 is apparent in FIG. 1B. Adhesive layer 120 is visible over the entirety of the device 100 except where absorbent stack 130 is present: absorbent stack 130 is situated over first portion 113 of the surface area 112 (not shown in FIG. 1B). Visible in this view is surface 133 of first absorbent layer 132. While FIG. 1B illustrates the adhesive layer 120 as generally square or rectangular in shape and the absorbent stack 130 as generally circular or cylindrical in shape, it can be appreciated that the adhesive layer and absorbent stack may be other shapes, including but not limited to, square, rectangular, circular or cylindrical, oval, ellipse, or etc.

Useful embodiments of this and other similar constructions of the vapor intrusion device rely on an arrangement of layers wherein a barrier layer and an adhesive layer combined as a backing provide an adhesive portion of the device and the absorbent stack is arranged such that it is transversely surrounded by the adhesive layer of the backing. The adhesive layer may be in direct contact with the absorbent stack and in some embodiments the construction substantially excludes direct contact between the absorbent stack and the barrier layer. In some embodiments, such as that shown in FIG. 1A, the adhesive layer 120 is in direct contact with absorbent stack 130 over the entire boundary between second absorbent layer 134 and adhesive layer 120. In some embodiments, the absorbent stack is in direct contact with the barrier layer; in other embodiments, a material or layer of material other than the adhesive is disposed between the absorbent stack and the barrier layer. Combinations of such arrangements are also possible.

In all embodiments of the vapor intrusion devices, the adhesive layer is arranged to provide an exposed adhesive surface transversely surrounding the absorbent stack. By "exposed" in this context, it is meant that the adhesive is available to provide adhesive contact to form an adhesive bond, for example a pressure sensitive adhesive bond, of the vapor intrusion device with a vapor intrusion substrate. In FIG. 1A, the exposed adhesive surface is indicated by 122. An exposed adhesive surface is in some embodiments covered by a release layer, which is a layer that contacts the adhesive layer directly but may be peeled off by hand to expose the adhesive layer to the atmosphere, further without substantially damaging or deforming the adhesive layer during the exposing.

Useful embodiments of this and other similar constructions of the vapor intrusion device further rely on dimensions and physical properties of the backing surrounding the absorbent stack to provide drape and conformation around the absorbent stack and further facilitate contact of the adhesive layer with a surface when the vapor intrusion device is applied thereto.

Figure 2:
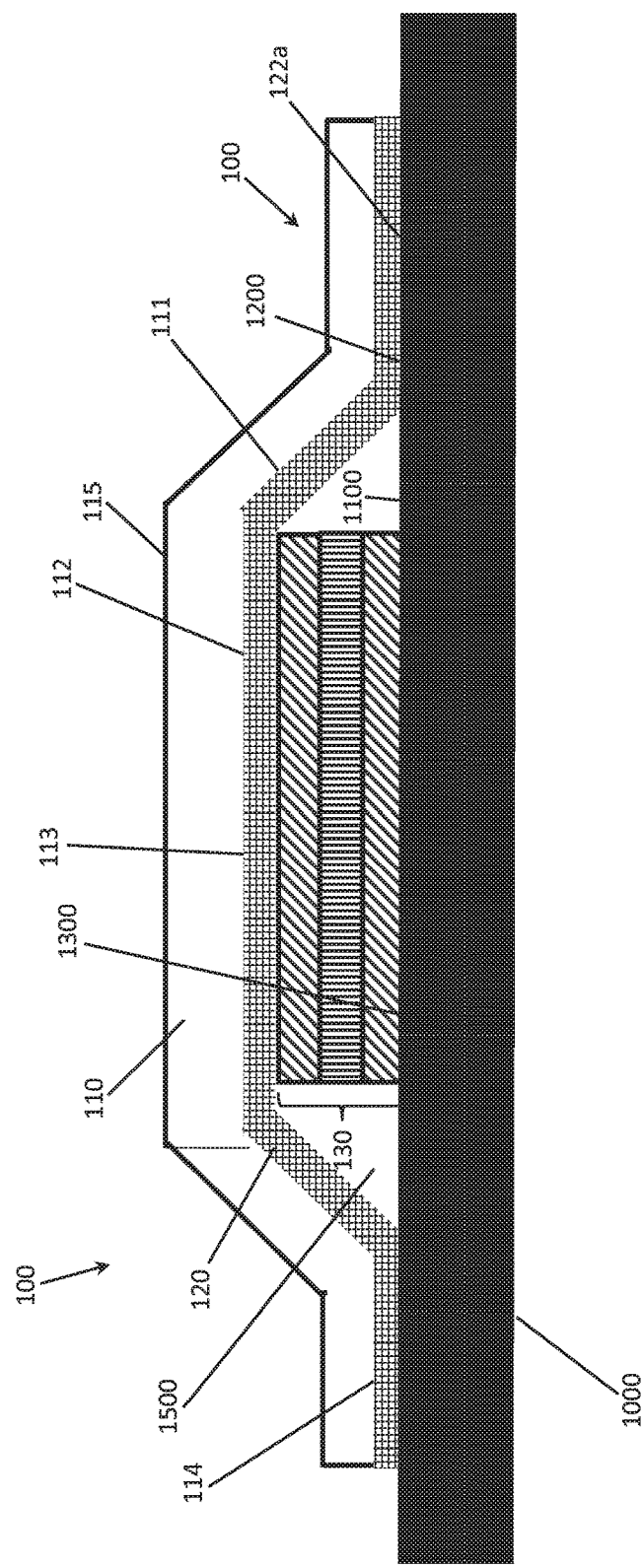
FIG. 2 is a schematic cutaway view of the vapor intrusion device of FIGS. 1A, 1B, further as applied to a substrate undergoing or suspected of undergoing vapor intrusion.

FIG. 2 shows a cutaway side view of the vapor intrusion device 100 of FIG. 1A applied to a vapor intrusion surface, wherein the value of the exposed adhesive surface 122 of FIG. 1A is made clear to one of ordinary skill. Vapor intrusion device 100 is applied to a first portion 1200 of a surface 1100 of a vapor intrusion substrate 1000. Substrate surface portion 1200 is contacted with an exposed adhesive surface 122 (as shown in FIG. 1A), and the exposed adhesive surface 122 of FIG. 1A becomes an adhesively sealed interface 122a as shown in FIG. 2. Adhesively sealed interface 122a defines the interface between adhesive layer 120 and vapor intrusion substrate surface portion 1200. Adhesively sealed interface 122a is characterized as substantially transversely surrounding absorbent stack 130.

Adhesively sealed interface 122a combined with the construction of device 100 applied to the substrate surface portion 1200 defines an enclosed volume that includes absorbent stack 130. Specifically, the adhesively sealed interface 122a, barrier layer 110, and surface portion 1200 together define a test volume 1500. Test volume 1500 includes absorbent stack 130. Barrier layer 110 is sufficiently flexible and conformable, and has suitable dimensions to form the adhesively sealed interface 122a transversely surrounding absorbent stack 130. Barrier layer 110 therefore includes adhesive layer 120 disposed in a manner suitable for adhesive application of the vapor intrusion device 100 to substrate surface portion 1200, wherein adhesively sealed interface 122a is formed transversely surrounding absorbent stack 130 where surface portion 1200 is contacted by exposed adhesive surface 122.

Further with regard to FIG. 2, adhesively sealed interface 122a is effective to produce and maintain direct and substantial contact of surface 133 of first absorbent layer 132 with a second surface portion 1300 of substrate 1000. In this manner, first absorbent layer 132 alone is directly exposed to a selected analyte diffusing through the substrate. Due to the physical separation of the absorbent layers 132, 134 by first spacer layer 136, second absorbent layer 134 is not directly exposed to the selected analyte diffusing through the substrate. Rather, second absorbent layer 134 is situated to absorb ambient amounts of the selected analyte present in test volume 1500. "Ambient analyte" means an analyte present within test volume 1500 that is not attributable to direct diffusion through the substrate and into first absorbent layer 132. Sources of ambient analyte include but are not limited to ambient atmosphere leaking into test volume 1500 via leaks in the substantially adhesively sealed interface 122a (that is, leaks due to imperfections in the adhesively sealed interface 122a), analyte diffusing into test volume 1500 through adhesive 120 and into test volume 1500, analyte diffusing through the substrate 1000 and into test volume 1500 but not into first absorbent layer 132, and analyte diffusing out of first absorbent layer 132.

Figure 3A:
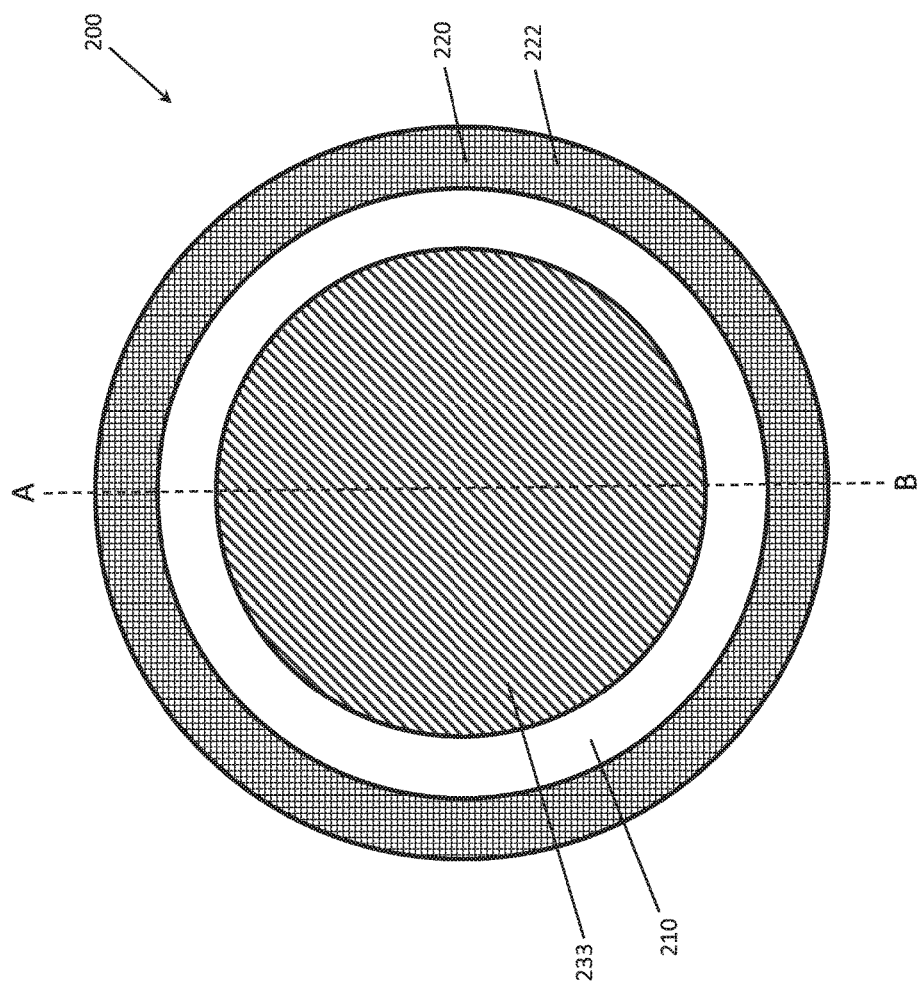
FIG. 3A is a schematic top view of another vapor intrusion device.
Figure 3B:
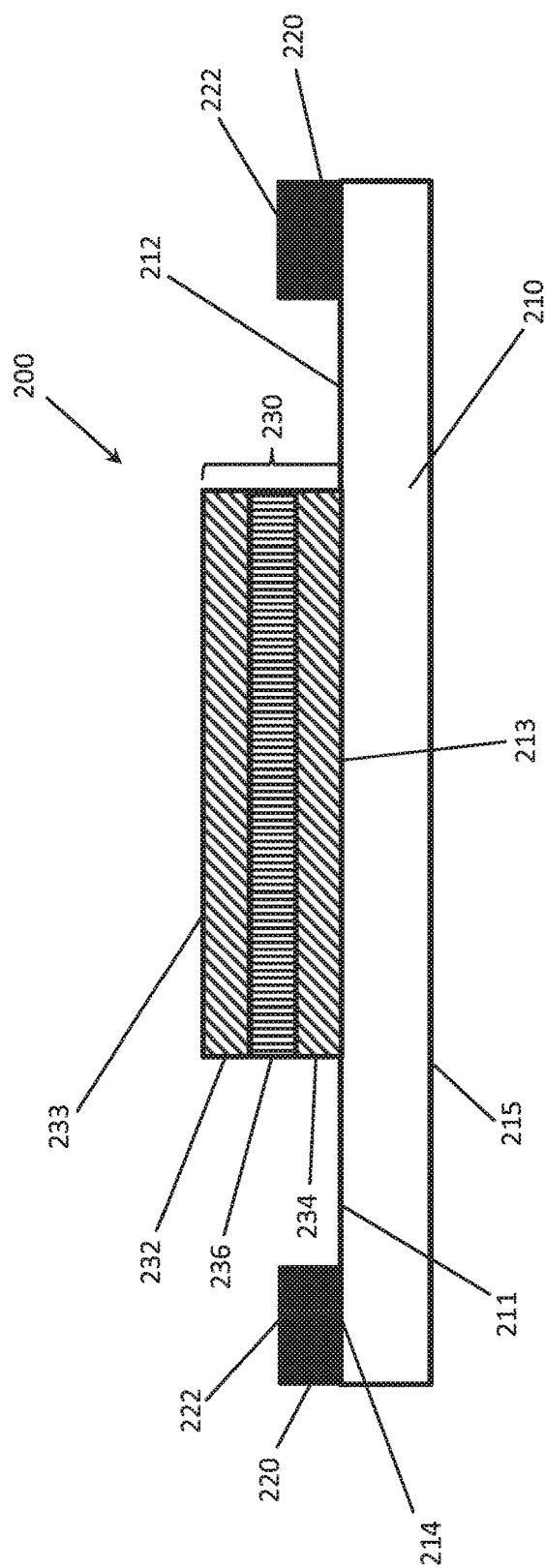
FIG. 3B is a schematic side view of the device of FIG. 3A taken through the line A-B.

The shape of the passive vapor intrusion device construction is not particularly limited. The exemplary but non-limiting embodiment of FIG. 1B shows barrier layer 110 as having a substantially square or rectangular shape and absorbent stack 130 as having a substantially circular shape. FIGS. 3A, 3B show another exemplary but non-limiting embodiment of the vapor intrusion device of the invention. In FIG. 3A, a top view of an overall circular construction of vapor intrusion device 200 is shown. Barrier layer 210 is visible between adhesive 220 that covers only the outer boundary portion of barrier layer first surface 212, and does not contact absorbent stack 230 (not visible except for first absorptive layer 232 surface 233). Thus, between adhesive 220 and absorbent stack 230, barrier layer first surface 212 is visible in the view of FIG. 3A.

FIG. 3B shows a side view of the device shown in FIG. 3A as divided along line A-B of FIG. 3A. In this view, placement of adhesive layer 220 exposed surface 222 is visible. Absorbent stack 230 is disposed over barrier layer 210 first side 211 on first portion of surface 213. Adhesive layer 220 is disposed over barrier layer 210 first side 211 on second portion of surface 214. Surface portions 213, 214 are mutually exclusive, that is, they do not overlap. In other embodiments, the adhesive layer 220 may extend to be flush with surface 233. That is, in some embodiments, there may not be a gap between adhesive layer 220 and surface 233.

Figure 4:
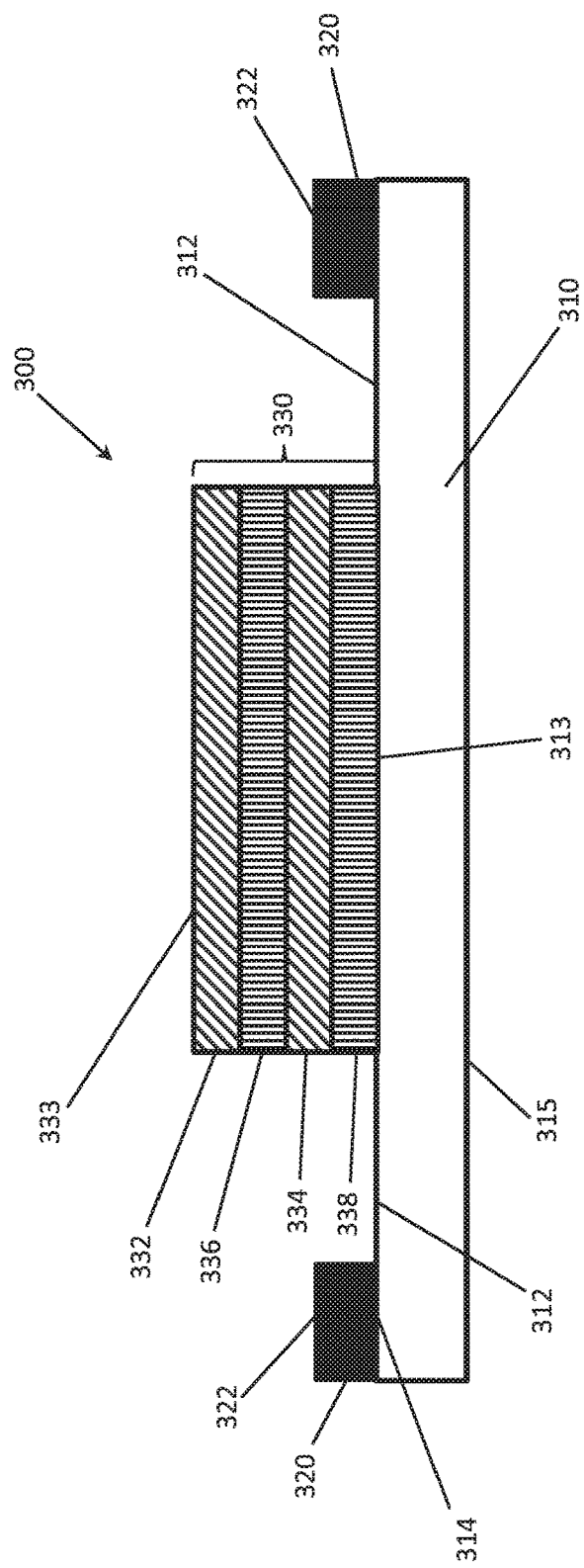
FIG. 4 is a schematic cutaway view of another vapor intrusion device.

FIG. 4 is another embodiment of vapor intrusion device. Device 300 is similar to device 200 of FIGS. 3A, 3B except that device 300 includes second spacer layer 338 disposed between second absorbent layer 334 and the first surface portion 313 of barrier layer 310.

Figure 5:
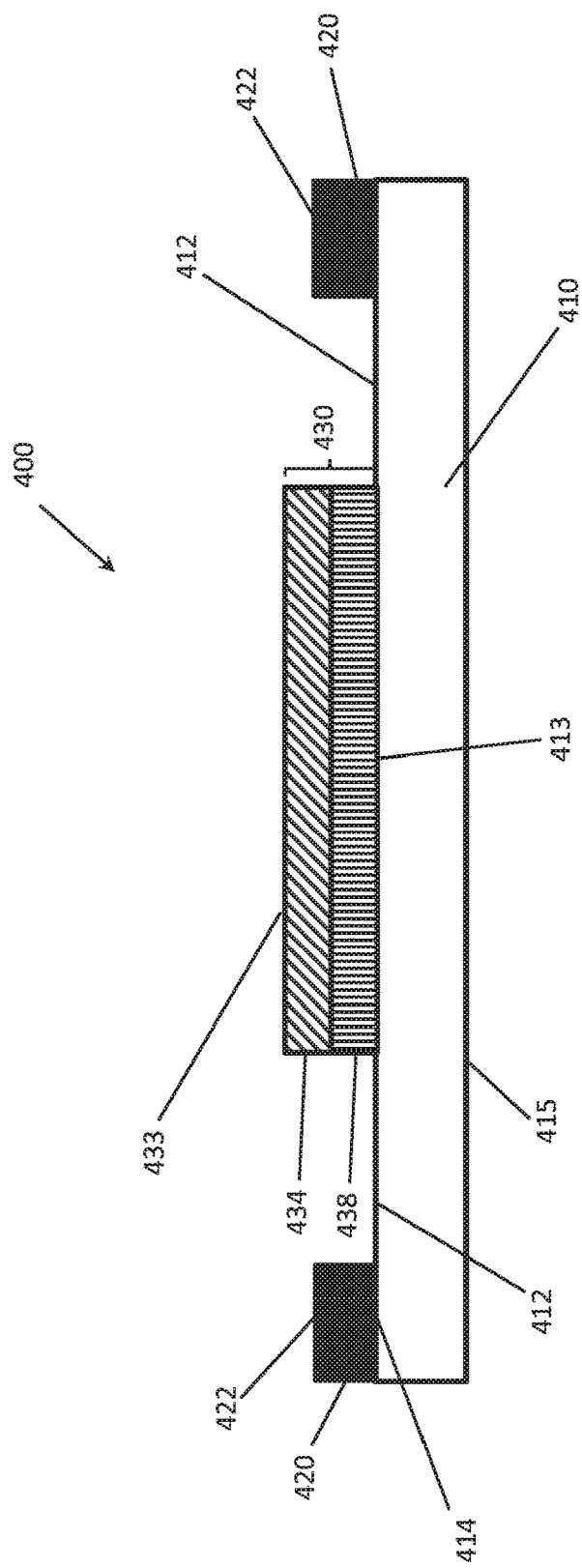
FIG. 5 is a schematic cutaway view of another vapor intrusion device.

FIG. 5 is another embodiment of vapor intrusion device. Device 400 is similar to device 300 of FIG. 4 except that device 400 includes only a single spacer layer 438 disposed between a single absorbent layer 434 on the first surface portion 413 of barrier layer 410.

Barrier layer (110, 210, 310, 410 and other embodiments described herein) is composed of a material or combination of materials that is impermeable or substantially impermeable to a selected analyte or group of selected analytes. Preferably, the barrier layer has flexibility, conformability, modulus, and other physical properties associated with pressure sensitive tape backings. A pressure sensitive adhesive backing is a substrate onto which a pressure sensitive adhesive is applied to form a pressure sensitive adhesive tape. In some embodiments, the barrier layer is includes one or more mixtures, composites, or alloys of materials. In some embodiments separately or in combination with mixtures, composites, or alloys of materials, the barrier layer includes two or more discrete layers of chemically different materials or different mixtures thereof. Where the barrier layer includes two or more discrete layers, the combined layers impart impermeability. In some embodiments, one or more of the layers do not individually impart impermeability. Suitable materials for inclusion in the barrier layer include polyesters, polyurethanes, polyimides, polyamides, and like polymeric materials and mixtures or alloys of two or more thereof and processed as a web-based film, sheet, or coating; metals such as aluminum, steel, copper, tin, and various alloys and mixtures thereof as well as layered and multilayered constructions thereof, in some embodiments with one or more polymeric materials as discussed above; glass or ceramic materials; and combinations of two or more of any of these materials in any configuration. In some embodiments the impermeable barrier layer is provided by coating an impermeable material onto a permeable barrier layer, or coating a material onto a barrier layer that renders the coated barrier layer impermeable. Where two or more materials are combined in a barrier layer, the combination may be a mixture, an alloy, a layered arrangement, or a combination thereof.

The barrier layer of the device is an impermeable, substantially planar substrate. In embodiments, the barrier layer is a web-based material having first and second major sides defining a web thickness. The barrier layer is not particularly limited as to thickness or overall dimensions except as to ease of use in obtaining adhesive contact between the adhesive and the selected surface for vapor intrusion analysis. Thickness of the barrier layer is also determined, in some embodiments, by the physical properties of modulus, flexural strength, and other material properties of the selected barrier layer. In embodiments, the barrier layer is about 25 microns (μm) to 3 millimeters (mm) thick, or about 50 μm to 3 mm, or about 100 μm to 3 mm, or about 25 μm to 2 mm, or about 25 μm to 1 mm, or about 50 μm to 1 mm, or about 100 μm to 1 mm thick. While not intended to be limiting as to the other two dimensions of the barrier layer, in some embodiments these dimensions range from 1 cm to 1 meter, for example about 2 cm to 1 meter, or about 3 cm to 1 meter, 4 cm to 1 meter, 5 cm to 1 meter, 6 cm to 1 meter, 7 cm to 1 meter, 8 cm to 1 meter, 9 cm to 1 meter, 10 cm to 1 meter, or about 1 cm to 90 cm, or about 1 cm to 80 cm, or about 1 cm to 70 cm, or about 1 cm to 60 cm, or about 1 cm to 50 cm, or about 1 cm to 40 cm, or about 1 cm to 30 cm, or about 1 cm to 20 cm, or about 1 cm to 10 cm, or about 3 cm to 10 cm, or about 3 cm to 8 cm.

The passive vapor intrusion device of the invention includes an absorbent stack (130, 230, 330, 430 and other embodiments described herein) disposed on a first portion of the barrier layer. The first portion of the surface area is less than the total surface area. The absorbent stack includes a first absorbent layer, a second absorbent layer (in some embodiments), a first spacer layer disposed between first and second absorbent layers, and a second spacer between the second absorbent layer and the barrier layer (in some embodiments). The first and second absorbent layers include absorbent materials. In some embodiments, the first and second absorbent layers include the same absorbent materials. In some embodiments, the first and second absorbent layers are substantially the same: that is, the absorbent materials included in the first and second absorbent layers are substantially the same and are present in substantially the same amounts in the first and second absorbent layers.

Suitable absorbent layers include any material or combination thereof having a partition coefficient for a selected analyte of at least 100, termed herein "absorbent material". The absorbent layer suitably comprises, consists essentially of, or consists of the absorbent material. Thus, the absorbent material may be from about 1 wt % to 100 wt % of each of the first and second absorbent layers, or about 5 wt % to 100 wt %, or about 10 wt % to 100 wt %, or about 20 wt % to 100 wt %, or about 30 wt % to 100 wt %, or about 40 wt % to 100 wt %, or about 50 wt % to 100 wt %, or about 60 wt % to 100 wt %, or about 70 wt % to 100 wt %, or about 80 wt % to 100 wt %, or about 90 wt % to 100 wt % of each of the first and second absorbent layers. While the absorbent material employed in the absorbent layers may suitably differ depending on the analyte selected for vapor intrusion testing, materials having broad suitability for a number of different commonly selected analytes may be selected for use as the absorbent material. One commonly employed absorbent material is activated carbon. Activated carbon is adsorbent to many VOCs of potential interest and has a high affinity therefor. The porous carbon particles are employed in a layer format by adhering or embedding the particles within a nonwoven or woven mat of fibers or a membrane. The mat or membrane is typically formed from a material such as polytetrafluoroethylene (PTFE) that does not tend to absorb or adsorb the selected analyte(s). Such carbon particulate loaded nonwovens are available for purchase for the purpose of scavenging or sampling organic compounds present in gaseous form. Examples of suitable activated carbon-loaded PTFE membranes include M566 Organic Vapor Sampling Media, available from Assay Technology of Livermore, Calif.; and adsorbent media employed in 3M® 3500B Organic Vapor Monitor, available from the 3M Company of Maplewood, Minn.

The absorbent layers are also suitably formed from a polymer or blend thereof that has a high affinity for the selected analyte. Silicone (polydimethyldisiloxane and related polymer) gels and crosslinked silicone elastomers, for example, are usefully employed as the absorbent material in some embodiments. The silicone polymer is suitably employed alone or in a blend or layered arrangement with one or more additional materials in an absorbent layer. Other polymeric absorbent materials are suitably employed in an absorbent layer depending on affinity for the selected analyte. Polymeric materials are suitably employed as coated or thermoformed into an absorbent layer. Blends thereof are also suitably employed, as are blends of absorbent polymers and activated carbon particles.

The thickness of the absorbent layers is not particularly limited. However, the absorbent layers are sufficiently thin to facilitate application of the vapor intrusion device to the selected surface in the manner described above, and provide for maintenance of the adhesively sealed interface between the device and the vapor intrusion substrate as described above and for the entirety of a test period (test period to be described along with methodology described below) wherein the device is adhered to the substrate and left undisturbed for a period of time. In embodiments, each absorbent layer is about 0.1 mm to 1 cm thick, or about 0.3 mm to 1 cm, or about 0.5 mm to 1.0 cm, or about 0.1 mm to 8 mm, or about 0.1 mm to 6 mm, or about 0.1 mm to 4 mm, or about 0.1 mm to 2 mm, or about 0.1 mm to 1 mm thick.

The minimum amount of absorbent material in each of the absorbent layers of the absorbent stack is determined by the absorptive or adsorptive capacity of the absorbent media for the analyte, the amount of absorbent media in each absorbent layer, the rate of diffusion of the selected analyte through the targeted substrate as a function of time, and the length of the testing period (that is, the amount of time the device is left undisturbed after applying to the substrate). In embodiments where the absorbent material is activated carbon, carbon particulate density of between 0.2 g/cm$^3$ and 1.0 g/cm$^3$ is often employed, such as 0.3 g/cm$^3$ to 1.0 g/cm$^3$, or about 0.4 g/cm$^3$ to 1.0 g/cm$^3$, or about 0.5 g/cm$^3$ to 1.0 g/cm$^3$, or about 0.6 g/cm$^3$ to 1.0 g/cm$^3$, or about 0.2 g/cm$^3$ to 0.9 g/cm$^3$, or about 0.2 g/cm$^3$ to 0.8 g/cm$^3$, or about 0.2 g/cm$^3$ to 0.7 g/cm$^3$, or about 0.2 g/cm$^3$ to 0.6 g/cm$^3$, or about 0.4 g/cm$^3$ to 0.8 g/cm$^3$ for media having thickness of about 0.1 mm to 1 cm, or about 0.2 mm to 1 cm, or about 0.3 mm to 1.0 cm, or about 0.1 mm to 0.8 mm, or about 0.1 mm to 0.6 mm, or about 0.1 mm to 0.4 mm, or about 0.2 mm to 0.6 mm, or about 0.2 mm to 0.4 mm.

The first spacer layer (136, 236, 336 and other embodiments described herein) is disposed between the first and second absorbent layers. In embodiments, a second spacer layer (e.g. layer 338 of FIG. 4) is further disposed between the barrier layer and the second absorbent layer. In embodiments, one effect of the first spacer layer is to physically separate the first and second absorbent layers in the absorbent stack. In embodiments, a second effect of both the first and second spacer layers is to facilitate individual collection each of the first and second absorbent layers from the vapor intrusion device after the test period. In this context, "collection" or "collecting" means human action taken to remove and isolate each of the first and second absorbent layers from the remainder of the device, wherein such action may be carried out without substantial damage or deformation of either the first or second absorbent layers. In embodiments, the substantial entirety of each of the first and second absorbent layers are obtained in this way; that is, the absorbent layers may be obtained individually and in their substantial entirety at the end of the test period. The ability to individually separate the absorbent layers after the test period is important for methods employing the vapor intrusion device, as will be discussed below.

With regard to the individual collecting of the first and second absorbent layers, the first and second spacer layers include one or more major surfaces thereof for contacting the absorbent media and adhering sufficiently to hold the absorbent stack in place during application thereof to a substrate, followed by hand peeling of the absorbent layers from the spacer layers after the device is removed from the substrate at the end of the test period. Thus, in some embodiments, one or more spacer layer surfaces include an adhesive on one or more major surfaces thereof while one or more absorbent layer major surfaces are suitable for hand peel release therefrom. In some other embodiments, one or more absorbent layer surfaces include an adhesive on one or more major surfaces thereof while one or more spacer layer major surfaces are suitable for hand peel release therefrom. Release with hand force may be inherent in one or more of the materials included in the spacer layers (such as PTFE membranes) or the absorbent layers; however, in some embodiments, a release material may be added to one or more major surfaces of the spacer layers or the absorbent layers in order to facilitate release. Release materials include silicone, PTFE, and hydrophobic organic polymers such as polyethylene and acrylate copolymers having C8-C40 ester groups and are often applied as coatings to one or more major sides of a layer, such as a barrier layer, a spacer layer, or an absorbent layer. In embodiments where the device does not include a second spacer layer, the barrier layer is in direct contact with the second absorbent layer and adhesion and subsequent collection of the second absorbent layer is facilitated in the same manner as the collection of absorbent layers described above: by providing substantial contact between major surfaces thereof with sufficient adhesion to maintain the contact until after the device is removed from a test substrate at the end of the test period.

The spacer layers are characterized by having a low affinity for the selected analyte(s). "Low affinity" means having a partition coefficient for the selected analyte(s) of less than 10, for example about 0.0001 to 10, or about 0.0001 to 1, or about 0.0001 to 0.1, or about 0.0001 to 0.01. The spacer layers are also characterized by the ability to physically separate and maintain the separation of the first and second absorbent layers throughout the test period and until the first and second absorbent layers are individually collected for analysis. In some embodiments the spacer layers may facilitate transverse vapor phase connectivity within the test volume and contact of the target analytes with the absorbent layers, whereas in other embodiments the spacers may serve as a barrier to the target analytes.

In some embodiments, suitable spacer layers include paper, Kraft paper, and other natural and synthetic woven or nonwoven mats. In some embodiments, the spacer layer is coated with a release material to facilitate release of the first and second absorbent layers from the device as discussed above. Adhesion of the absorbent layers, the one or two spacer layers, and the barrier layer (optionally with adhesive applied between the barrier layer and the absorbent stack) may be minimally sufficient to hold the absorbent stack together as assembled through the test period and also to hold the vapor intrusion device assembly as assembled through the test period. Materials other than paper are also useful to form the spacer layers. Any of the barrier layer materials listed above may be suitably employed as a spacer layer in the absorbent stack.

The passive vapor intrusion device of the invention includes an adhesive layer (120, 220, 320, 420 and other embodiments described herein) disposed on at least a portion of the barrier layer surface. The adhesive is disposed to transversely surround the absorbent stack. The adhesive layer may extend substantially over the entire surface of the first major side of the barrier layer, as shown in FIGS. 1A, 1B, and 2 as well as other embodiments thereof, or only over a portion thereof, as shown in FIGS. 3A, 3B, 4, 5 and other embodiments thereof. In all cases, adhesive placement on the barrier layer surface is selected to enable an adhesively sealed interface as described above. The functionality of the adhesive in forming an adhesively sealed interface (e.g. 122a of FIG. 2) is dispositive with regard to placement thereof on the barrier layer. Thickness of the adhesive layer is not particularly limited but often is about 10 µm to 1 mm thick, or about 20 µm to 1 mm thick, or about 30 µm to 1 mm thick, or about 40 µm to 1 mm thick, or about 50 µm to 1 mm thick, or about 60 µm to 1 mm thick, or about 70 µm to 1 mm thick, or about 80 µm to 1 mm thick, or about 90 µm to 1 mm thick, or about 100 µm to 1 mm thick, or about 10 µm to 800 µm thick, or about 10 µm to 600 µm thick, or about 10 µm to 500 µm thick, or about 10 µm to 400 µm thick, or about 10 µm to 300 µm thick, or about 10 µm to 200 µm thick, or about 10 µm to 100 µm thick, or about 25 µm to 250 µm thick, or about 25 µm to 200 µm thick, or about 25 µm to 150 µm thick. Thickness of the adhesive layer is selected along with adhesive material selection and an understanding of the adhesive needs of the intended test substrate in order to design and facilitate a device that will form the intended adhesively sealed interface between the device and the intended test substrate.

Materials suitably employed as the adhesive layer include any material known to form an adhesive bond between the targeted substrate for vapor intrusion testing and the barrier layer employed in the vapor intrusion device. In some embodiments, the adhesive has a low affinity for one or more selected analytes; however, this is not necessary for operation of the vapor intrusion device to work as intended. In some embodiments, the adhesive is a pressure sensitive adhesive. Pressure sensitive adhesives include acrylate adhesives such as acrylic acid copolymers of C8-C20 acrylate esters and natural and synthetic rubber adhesives. Also useful are reactive sealants such as curable silicone and epoxy adhesives; however, these are often less useful than pressure sensitive adhesives because reactive sealants tend to prevent subsequent clean removal of the vapor intrusion device from the target substrate upon completion of the test. Clean removal of the vapor intrusion device from the targeted substrate in a single piece at the end of the test period, further without causing undue damage or distortion of the absorbent stack by the removal, is advantageous with regard to the subsequent analysis of analyte quantification of the first and second absorbent layers. Analyte quantification is the purpose of the test methods described below and to complete the vapor intrusion test of the invention; to achieve this purpose, the absorbent layers are obtained individually at the end of the test substantially without damage or deformation as will be described below. Further, while the absorbent layer(s) may be separated for analysis, the device and its component parts (e.g., the absorbents layer(s), the barrier layer(s), the adhesive layer(s), etc.) may be manufactured, packaged and/or sold as a single unit or manufactured, packaged and/or sold as individual component parts with instructions for assembly. In embodiments, the device is a single unit.

Method of Quantifying Passive Vapor Intrusion

Also disclosed herein is a method of quantifying the amount (or rate) of diffusion of selected analyte through a targeted substrate having or suspected of having a selected analyte diffusing therethrough. The method includes applying a vapor intrusion device as described above to the surface of a targeted substrate, wherein the applying includes directly and substantially contacting the first absorbent layer (132 and other embodiments described herein) with the substrate; forming an adhesively sealed interface (122a and other embodiments described herein) between the adhesive layer of the device to define a test volume, the test volume including the absorbent stack therein; maintaining the adhesively sealed interface for a period of time; removing the device from the substrate; dividing the absorbent stack in a manner suitable to isolate each of the first and second absorbent layers; analyzing the amount of the analyte in the first absorbent layer; analyzing the amount of the analyte in the second absorbent layer; and subtracting the amount of the analyte in the second absorbent layer from the amount of the compound in the first absorbent layer to yield data on the rate of vapor intrusion of the analyte. In some embodiments, a second absorbent layer may not be utilized, such as in cases where the concentration of the target analyte(s) in the ambient environment would result in a negligible amount of analyte in the second absorbent layer compared to the first.

The amount of time suitable for maintaining the adhesively sealed interface is called the test period. The test period is suitably determined by the user. The test period is based on the expected rate of diffusion of the selected analyte through the targeted substrate, the amount of absorbent materials in the absorbent layers, and affinity of the absorbent materials for the selected analyte. In each case, the test period is at least a sufficient period of time to accumulate a measurable quantity of the selected analyte in the first absorbent layer. The user can also determine the appropriate size of device required to achieve a measurable quantity of the selected analyte in the desired test period. In embodiments, the test period is about 10 minutes to 30 days or 1 month, or about 10 minutes to 25 days, or about 10 minutes to 20 days, or about 10 minutes to 15 days, or about 10 minutes to 10 days, or about 10 minutes to 7 days, or about 10 minutes to 6 days, or about 10 minutes to 5 days, or about 10 minutes to 4 days, or about 10 minutes to 3 days, or about 10 minutes to 2 days, or about 10 minutes to 24 hours or about 10 minutes to 12 hours, or about 10 minutes to 6 hours, or about 10 minutes to 5 hours, or about 10 minutes to 4 hours, or about 10 minutes to 3 hours, or about 10 minutes to 2 hours, or about 10 minutes to 1 hour, or about 10 minutes to 2 hours, or about 10 minutes to 3 hours, or about 10 minutes to 4 hours, or about 30 minutes to 7 days, or about 1 hour to 7 days, or about 1 hour to 3 days, or about 1 hour to 24 hours, or about 6 hours to 24 hours, or about 1 hour to 12 hours, or about 1 hour to 6 hours, or about 6 hours to 12 hours.

When a "clean" (i.e. not loaded with a selected analyte) absorbent layer is initially contacted with a solid medium containing an analyte, such as the direct contact between the device first absorbent layer and the targeted substrate, the concentration of the analyte is relatively high in the medium and is zero or substantially zero at the surface of the absorbent layer. This difference creates a driving force moving the analyte from the media to the absorbent layer for capture following Fick's law. If the device is operating under Fick's law, its mass collection over time will increase linearly with the sampling rate. The absorbent layers, present within the test volume for the test period, takes advantage of Fick's law to accumulate the targeted analyte within the first absorbent layer.

The second absorbent layer, as it is not in direct contact with the targeted vapor intrusion substrate and further not in direct contact with the first absorbent layer, is not available for direct diffusion of the analyte from the targeted substrate. Rather, the second absorbent layer collects only ambient analyte, as is discussed above. At the same time, the first absorbent layer collects both selected analyte diffusing through the targeted substrate, also termed "flux" herein, plus ambient analyte from the sources thereof as discussed above. This arrangement is the source of accuracy of the passive vapor intrusion device of the invention: by determining the concentration of the selected analyte individually in each of the first and second absorbent layers at the end of a known test period, and subtracting the concentration of analyte in the second absorbent layer from the concentration of analyte in the first absorbent layer, an accurate determination of the rate of vapor intrusion is made. The importance of the second adsorbent layer to correct for the presence of the target analyte in ambient air increases as the relative concentration in the ambient air increases, and in most vapor intrusion investigations the concentration of the target analyte in ambient air is not typically known a priori. Determination of concentration of analyte in each layer is accomplished using analytical chemistry. Such determinations are the subject of test protocols, extraction methods, and analyte quantification provided by a qualified analytical laboratory. It is imperative that appropriate analytical protocols are selected and developed with the analytical laboratory with respect to the type of materials used in the absorbent layers and expected mass loading. Highly efficient extraction methods, such as thermal desorption, may be required in cases where expected mass loading is low in order to achieve a measurable result.

The analyte selected for analysis is a compound that has sufficient volatility to partition from a source to the gaseous state and migrate in the gaseous state to contact a passive vapor intrusion device, further wherein the compound is selected or targeted for vapor intrusion analysis. The first and second absorbent layers are further selected for partition coefficient with respect to the selected analyte. The list of potential analytes advantageously measured using the devices and methodology discussed herein is extensive; guidance to chemicals encountered in vapor intrusion is found at https://www.epa.gov/vaporintrusion.

Using the devices and methods of the invention, the contribution of ambient analyte is excluded from passive vapor intrusion measurement. The device of the invention, coupled with the above described method of analysis, is a complete solution to the problem of how to easily, reproducibly, and accurately quantify vapor intrusion passively using a simple, inexpensive construction and otherwise standard quantification methodology.

EXPERIMENTAL

The following experimental data is not intended to be limiting and merely sets forth some of the many possible embodiments for the appended claims.

Sample preparation procedure. Vapor intrusion sampling devices are prepared by cutting a 26 mm diameter circle from a section of NASHUA® 322 Multi-Purpose Foil Tape (2.0 mil Al foil coated with 3.0 mils of a low-VOC synthetic rubber adhesive and having an unbleached natural Kraft paper liner protecting the adhesive side of the tape; obtained from Berry Plastics Corp. of Evansville, Ind.) to form a backing (combined barrier layer and adhesive layer). The two absorbent layers consist of 19 mm diameter circlular M566 Organic Vapor Sampling Media (obtained from Assay Technology of Livermore, Calif.). Then, two spacer layers are obtained by cutting two, 19 mm diameter circles of plain copy paper, 30% recycled content, from 8.5"×11" sheets. An absorbent stack is formed by contacting each of the absorbent layers and each of the spacer layers in alternating order. Finally, the absorbent stack is contacted with the adhesive side of the foil tape, wherein the paper-surface side of the stack is contacted with the adhesive side of the aluminum tape substantially in or proximal to the center thereof.

Test apparatus. A test apparatus includes an upper chamber and a lower chamber separated by a concrete specimen. A source of liquid heptane is added to the cylindrical lower chamber, and the lower chamber is enclosed by adding a 7 cm diameter by 3.8 cm long concrete cylinder to the top of the lower chamber. The bottom of the concrete cylinder is thus in direct contact with the headspace of the lower chamber, and the lower chamber is otherwise sealed by addition of the concrete. At ambient laboratory temperature, the heptane concentration in the headspace of the lower chamber equilibrates to be about 40,000 ppbv. The rate of diffusion of heptane (flux) through concrete at steady state is known to be 40 $g/m^2/day$. It will be understood that other analytes are suitably employed but the amount thereof accumulating in the lower chamber will differ with temperature and partial pressure of the analyte. An upper chamber is then added to the top of the concrete cylinder. The upper chamber is fitted with an inlet and outlet for gas. The upper chamber was continuously flushed with fresh air at a flow rate of approximately 60 mL/min. The air discharged from flushing the upper chamber was captured in a Tedlar® bag for analysis by a photoionization detector (PID). Under these conditions it took 17 days until the flux achieved steady state at the rate noted above and testing of the passive sampling device was initiated. Once steady state was achieved, the air discharged from the upper chamber was loaded with about 400 ppbv heptane. The amount of heptane in the upper chamber is easily varied for analysis purposes but the air flow should be such that the concentration in the upper chamber is at least two orders of magnitude lower than the concentration of analyte present in the bottom chamber. Once the device is applied, the concentration in the upper chamber will decrease as a result of the captured mass in the device. Based on the steady state flux rate before application of the device, and the cross-sectional area of the absorbent layer of the device, a calculation can be made of the expected mass capture of the device given its time of application and assuming 100 percent capture efficiency. This "target" level of mass uptake can then be compared to what is measured on the absorbent layer(s) upon extraction and subsequent analysis.

Test procedure. To test a passive vapor intrusion sampling device, the device is adhered to the top of the concrete cylinder of the test apparatus in a manner sufficient to form an adhesively sealed interface on the top of the cylinder and surrounding the absorbent stack of the sampling device, while providing substantial direct contact of the first absorbent layer of the absorbent stack with the surface of the concrete. The concrete cylinder is mounted on the lower chamber of the test apparatus, and the upper chamber of the test apparatus is applied over the cylinder and the device. The device mounted within the test apparatus is left undisturbed for a selected period of time. Access to the top chamber is achieved, and the device is removed from the surface of the concrete by hand, i.e. by peeling the first absorbent layer from the spacer layer, peeling the spacer layer from the second absorbent layer, and peeling the second absorbent layer from the second spacer layer or the barrier layer. The first and second absorbent layers are thus obtained substantially intact and are isolated for analysis. If analysis is not conducted immediately after the test is complete, the first and second absorbent layers are placed in separate sealed glass containers until such time as analysis can be conducted. Testing revealed that storage in sealed glass containers for a 2 week period did not significantly affect the results.

Analyte (the vapor intrusion compound selected for analysis) concentration individually within each of the first and second absorbent layers is measured by extraction of each layer with $CS_2$ plus an appropriate cosolvent, using procedures OSHA 7, NIOSH 1500, NIOSH 1550, and/or NIOSH 1604 for extraction. Extraction is followed by analysis using gas chromatography equipped with flame ionization detector (GC/FID).

EXAMPLES

Vapor intrusion sampling devices were prepared and tested according to the procedures above. Sample 1 is a control-one absorbent layer. Sample 2 is two absorbent layers with paper spacer layer in between. Sample 3 is two absorbent layers without spacer layer in between. Sample 4 is two absorbent layers with aluminum spacer layer in between The first absorbent layer of each device, that is, the absorbent layer that is in direct contact with the concrete during the test, is termed "A" in Table 1, and the second absorbent layer (not contacted with the concrete) is termed "B" in Table 1. In each of the test results shown in Table 1, expected and measured amount of heptane was compared to result in the reported ratio.

TABLE 1

Results of testing four passive vapor intrusion devices formed and tested as described. The results generally showed that the absorptive layer in contact with the concrete "A" absorbed more mass than expected based on the flux that was occurring before the device was applied. This discrepancy could be accounted for by subtracting the mass absorbed by the absorptive layer not in contact with the concrete "B". In some test runs, uncontrolled temperature variations occurred and were the suspected cause of the results where the actual:target ratios significantly varied from 1.

| Sample ID | Test Duration [hr] | Actual Heptane Mass [µg] | Target Heptane Mass [µg] | Actual:Target |
|---|---|---|---|---|
| CON A | 2.3 | 1522 | 1133 | 1.34 |
| 1B | 2.5 | 366 | 1004 | 0.36 |
| 1A | 2.4 | 1193 | 1004 | 1.19 |
|  |  | A − B = 827 |  | (0.83) |
| 2B | 2.5 | 225 | 830 | 0.27 |
| 2A | 2.5 | 1148 | 830 | 1.38 |
|  |  | A − B = 923 |  | (1.11) |
| 3B | 1.9 | 106 | 636 | 0.17 |
| 3A | 1.9 | 878 | 636 | 1.38 |
|  |  | A − B = 772 |  | (1.21) |
| 1B | 2.1 | 146 | 590 | 0.25 |
| 1A | 2.1 | 750 | 590 | 1.27 |
|  |  | A − B = 604 |  | (1.02) |
| 2B | 2.7 | 168 | 987 | 0.17 |
| 2A | 2.7 | 979 | 987 | 0.99 |
|  |  | A − B = 811 |  | (0.82) |
| 3B | 2.5 | 155 | 1244 | 0.12 |
| 3A | 2.5 | 766 | 1244 | 0.62 |
|  |  | A − B = 611 |  | (0.50) |
| 1A | 2.0 | 694 | 562 | 1.23 |
| 1B | 2.0 | 62 | 562 | 0.11 |
|  |  | A − B = 632 |  | (1.12) |
| 2A | 2.1 | 681 | 446 | 1.53 |
| 2B | 2.1 | 11 | 446 | 0.03 |
|  |  | A − B = 670 |  | (1.50) |
| 3A | 2.0 | 672 | 545 | 1.23 |
| 3B | 2.0 | 113 | 545 | 0.21 |
|  |  | A − B = 559 |  | (1.02) |

We claim:
1. A passive vapor intrusion sampling device comprising:
a barrier layer having first and second major sides;
an absorbent stack disposed over a first portion of a surface of the first major side of the barrier layer, the absorbent stack comprising:
a first absorbent layer, and
a first spacer layer disposed between the first absorbent layer and the barrier layer; and
an adhesive layer disposed on a second portion of the surface area of the first major side of the barrier layer and transversely surrounding the absorbent stack.

2. The device of claim 1 further comprising a second absorbent layer and a second spacer layer disposed between the first and second absorbent layers.

3. The device of claim 1 wherein the barrier layer is impermeable to an analyte selected for vapor intrusion analysis.

4. The device of claim 1 wherein the adhesive layer is disposed substantially over the entirety of the surface of the first major side of the barrier layer.

5. The device of claim 1 wherein the first portion of the surface of the first major side of the barrier layer is exclusive of the second portion of the surface of the first major side of the barrier layer.

6. The device of claim 2 wherein the first and second absorbent layers comprise substantially the same absorbent material, and the absorbent material is present in substantially the same amount in the first and second absorbent layers.

7. The device of claim 2 wherein the first and second absorbent layers comprise different absorbent material, and the absorbent material is present in substantially the same amount in the first and second absorbent layers.

8. The device of claim 1 wherein the first absorbent layer comprises activated carbon.

9. The device of claim 2 wherein the first and/or second absorbent layers comprise activated carbon.

10. The device of claim 1 wherein the partition coefficient of the first absorbent layer and the second absorbent layer is 100 or greater as to between the substrate and the absorbent layers.

11. The device of claim 1 wherein the device is a single unit.

12. A method of passive vapor intrusion measurement, the method comprising:
applying a passive vapor sampling device according to claim 1 to the surface of a solid substrate, wherein the applying comprises substantially contacting the first absorbent layer of the device with the substrate surface and forming an adhesively sealed interface therewith, the adhesively sealed interface transversely surrounding the absorbent stack of the passive vapor sampling device;
allowing a selected period of time to elapse;
removing the passive vapor sampling device from the substrate surface;
collecting the first absorbent layer;
analyzing the amount of a selected analyte in the first absorbent layer;
calculating the vapor intrusion mass flux measured by the device based on the mass of compound absorbed, time of application, and size of exposed absorbent layer.

13. A method of passive vapor intrusion measurement, the method comprising:
applying a passive vapor sampling device according to claim 2 to the surface of a solid substrate, wherein the applying comprises substantially contacting the first absorbent layer of the device with the substrate surface and forming an adhesively sealed interface therewith, the adhesively sealed interface transversely surrounding the absorbent stack of the passive vapor sampling device;

allowing a selected period of time to elapse;

removing the passive vapor sampling device from the substrate surface;

collecting the first and second absorbent layers;

analyzing the amount of a selected analyte in the first absorbent layer;

analyzing the amount of the selected analyte in the second absorbent layer;

subtracting the amount of the compound in the first absorbent layer from the amount of the compound in the second absorbent layer; and calculating the vapor intrusion mass flux measured by the device based on the mass of compound absorbed, time of application, and size of exposed absorbent layer.

14. The method of claim 12 wherein the selected period of time is about 10 minutes to one month.

15. The method of claim 13 wherein the selected period of time is about 10 minutes to one month.

16. The method of claim 12 wherein the substrate is a solid surface.

17. The method of claim 16 wherein the solid surface comprises concrete, cement, tile, or a combination of two or more thereof.

18. The method of claim 16 wherein the solid surface is a floor, slab, wall or ground surface.

19. The method of claim 13 wherein the substrate is a solid surface.

20. The method of claim 19 wherein the solid surface comprises concrete, cement, tile, or a combination of two or more thereof.

* * * * *